(12) United States Patent
Bert et al.

(10) Patent No.: US 8,809,814 B2
(45) Date of Patent: Aug. 19, 2014

(54) IRRADIATION OR IRRADIATION PLANNING SYSTEM FOR A RESCANNING METHOD USING A PARTICLE BEAM

(75) Inventors: Christoph Bert, Aschaffenburg (DE); Eike Rietzel, Weiterstadt (DE)

(73) Assignees: Siemens Aktiengesellschaft, München (DE); GSI Helmholtzzentrum für Schwerionenforschung GmbH, Darmstadt (DE)

( * ) Notice: Subject to any disclaimer, the term of this patent is extended or adjusted under 35 U.S.C. 154(b) by 0 days.

(21) Appl. No.: 13/384,232

(22) PCT Filed: Jun. 18, 2010

(86) PCT No.: PCT/EP2010/058636
§ 371 (c)(1),
(2), (4) Date: Apr. 2, 2012

(87) PCT Pub. No.: WO2011/006733
PCT Pub. Date: Jan. 20, 2011

(65) Prior Publication Data
US 2012/0187314 A1    Jul. 26, 2012

(30) Foreign Application Priority Data
Jul. 15, 2009    (DE) .......................... 10 2009 033 297

(51) Int. Cl.
*A61N 5/10*    (2006.01)
(52) U.S. Cl.
CPC .................................. *A61N 5/1031* (2013.01)
USPC ....................................................... 250/492.3
(58) Field of Classification Search
CPC ....... A61N 5/10; A61N 5/103; A61N 5/1031; A61N 5/1038
USPC ....................................................... 250/492.3
See application file for complete search history.

(56) References Cited

U.S. PATENT DOCUMENTS

2008/0078942 A1    4/2008    Rietzel

FOREIGN PATENT DOCUMENTS

DE    102005063220 A1    6/2007
DE    10 2008 027 485 A1    12/2009
(Continued)

OTHER PUBLICATIONS

Pardo et al., 'Heurestic Optimization of the Scanning Path of Particle Therapy Beams', Jun. 2009, Med. Phys. 36 (6), p. 2043-2051.*
(Continued)

*Primary Examiner* — Jack Berman
*Assistant Examiner* — Eliza Osenbaugh-Stewar
(74) *Attorney, Agent, or Firm* — Lempia Summerfield Katz LLC

(57) ABSTRACT

A method for irradiating a target volume includes defining a target region having a plurality of target points. The target points are individually approachable. The method includes defining a number of rescanning passes, in which the target region is scanned multiple times, such that the plurality of target points of the target region is approached variously often during the rescanning passes. At least some target points of the plurality of target points are not approached in all of the rescanning passes. The approaching of the plurality of target points is distributed among the rescanning passes such that for a target point of the plurality of target points that is not approached in all of the rescanning passes, at least one further rescanning pass, in which the target point is not approached, is located before a final rescanning pass, in which the target point is approached.

21 Claims, 5 Drawing Sheets

(56) References Cited

FOREIGN PATENT DOCUMENTS

| JP | 2001212253 A | 8/2001 |
|---|---|---|
| WO | WO 2009/040117 A1 | 4/2009 |
| WO | WO 2009/149882 A1 | 12/2009 |

OTHER PUBLICATIONS

PCT Written Opinion and Search Report dated Oct. 5, 2010 for corresponding PCT/EP2010/058636 with English translation.

Zenklusen, S., et al., "Preliminary Investigation for Developing Repainted Beam Scanning on the PSI Gantry 2," Paul Scherrer Institut (PSI), pp. 2-13 (2008).

Saito, N., et al., "Speed and Accuracy of a Beam Tracking System for Treatment of Moving Targets with Scanned Ion Beams," Physics in Medicine and Biology, vol. 54, pp. 4849-4862 (2009).

Chinese Office Action dated Feb. 7, 2014 for corresponding Chinese Patent Application No. 201080036718.6 with English translation.

M. Durante, et al., "Charged particles in radiation oncology," Nature Reviews Clinical Oncology, vol. 7, pp. 37-43, 2010.

\* cited by examiner

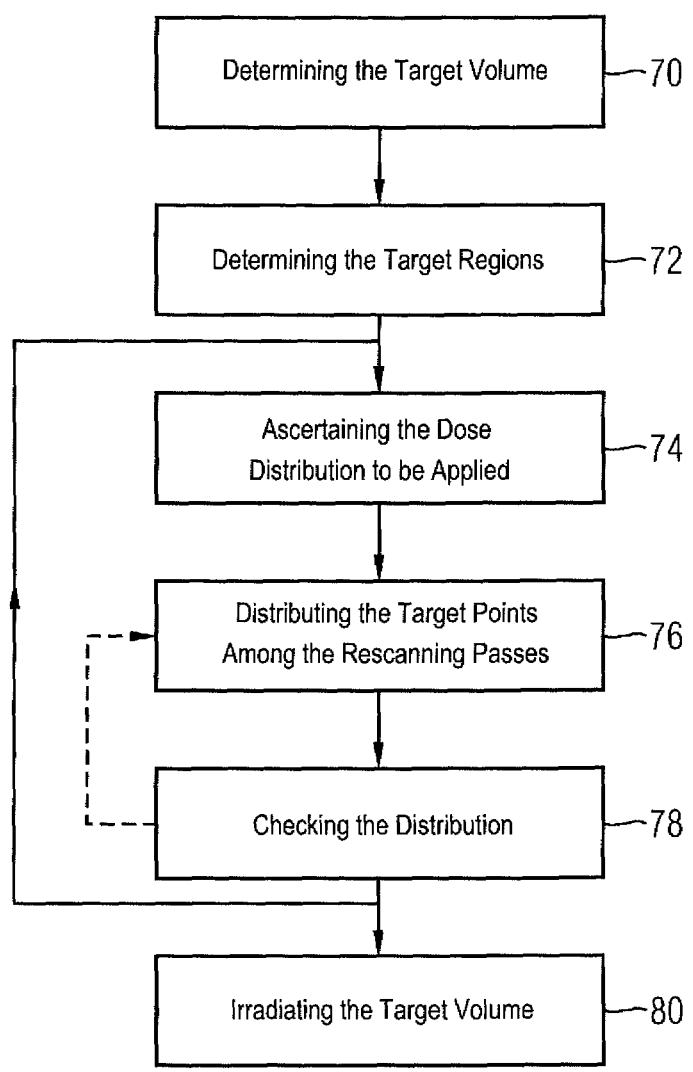

IRRADIATION OR IRRADIATION PLANNING SYSTEM FOR A RESCANNING METHOD USING A PARTICLE BEAM

The present patent document is a §371 nationalization of PCT Application Ser. No. PCT/EP2010/058636, filed on Jun. 18, 2010, designating the United States, which is hereby incorporated by reference. This patent document also claims the benefit of DE 10 2009 033 297.9, filed Jul. 15, 2009, which is also hereby incorporated by reference.

BACKGROUND

The present embodiments relate to a method for irradiation planning of a target volume and a method for irradiating a target region in a target volume.

Particle therapy is an established method for treating tissue (e.g., in tumor diseases). Irradiation methods of the kind employed in particle therapy are also used in non-therapeutic fields. For example, the non-therapeutic fields include research work such as for product development in the context of particle therapy done on inanimate phantoms or bodies, irradiation of materials, and so forth.

In these, charged particles such as protons, carbon ions, or other ions are accelerated to high energy levels, shaped into a particle beam, and carried via a high-energy transportation system to one or more irradiation chambers. In the irradiation chamber, the target volume to be irradiated is irradiated with the particle beam.

In the course of this, the target volume to be irradiated may move. For example, when a patient is being irradiated, motion of the patient while breathing may cause the tumor that is to be irradiated to move. Such a movement may also be simulated for research purposes by using model objects (e.g., phantoms).

In irradiation methods, in which many irradiation doses are to be deposited successively at different sites in the target volume and hence with a scanned particle beam, it is difficult to achieve a desired homogeneous dose distribution in the target volume if the target volume moves during the course of the irradiation.

With a scanned particle beam, the dose that is to be applied may be distributed among a plurality of passes. This method is also known as "rescanning." A target region is approached multiple times. At the target region, the total dose is built up successively by a plurality of repeatedly applied individual doses during the rescanning passes. This has the advantage that errors in the dose deposition, which in the event of a single pass would lead to a completely mistakenly applied dose, are averaged out to a certain degree by the multiple rescanning passes. Uncertainties about the position of the target volume, movements of the target volume, and so forth, may thus be at least partially compensated for.

For improving this, the published presentation by Silvan Zenklusen, et al., titled "Preliminary investigation for developing repainted beam scanning on the psi gantry 2," proposes that at each target point of a region that is scanned multiple times in a plurality of rescanning passes, in each rescanning pass, a dose that is less than an upper limit (e.g., an "upper dose limit") is always applied. A target point is irradiated in consecutive rescanning passes until a set-point dose has been reached. In the ensuing rescanning passes, the target point is excluded form a further irradiation (e.g., the target point is no longer approached).

SUMMARY AND DESCRIPTION

The present embodiments may obviate one or more of the drawbacks or limitations in the related art. For example, a method for irradiation planning or a method for irradiation that permits fast, advantageous triggering of an irradiation system in the rescanning is provided.

The following description of the individual features relates to both the device and the method without explicit mention thereof in each case. The individual features disclosed may also be used in other combinations than those shown.

One embodiment of a method for planning the irradiation of a target volume includes defining a target region having individually approachable target points. The method also includes defining a number of rescanning passes, in which the target region is scanned multiple times, such that the target points of the target regions are approached variously often during the rescanning passes. As a result, at least some of the target points are not approached in every rescanning pass. The approaching of the target points is distributed among the rescanning passes such that for at least one target point that is not approached in every rescanning pass, at least one further rescanning pass, in which the at least one target point is not approached, is located before a final rescanning pass, in which the at least one target point is approached.

The target volume to be irradiated may be divided up among a plurality of target regions. During an irradiation session, the plurality of target regions is irradiated in the rescanning process. Each target region of the plurality of target regions is irradiated in a plurality of rescanning passes. The plurality of target regions may be scanned successively. As soon as one target region has been scanned in the rescanning process, the next target region is scanned in the rescanning process, and so forth.

In one embodiment, the dose distribution that is defined for the target region may be nonhomogeneous. Even if the total dose that is to be applied for the target region has a homogenous dose distribution, it may be necessary for the dose distribution to be applied to be nonhomogeneous for one target region. During the irradiation of other target regions, parts of the target region are already occupied with a preliminary dose. The dose distribution may represent a measure for the particle beam to be applied. Taking into account planning specifications regarding the target volume, the dose to be deposited in the target volume, and/or the effective action of the dose deposited in the tissue, which may be characterized, for example, by stating the relative biological effectiveness (RBE), may be ascertained in a planning phase.

In one embodiment of the method, the dose distribution for the target region is applied by approaching the target points of the target region variously often during the rescanning passes. The phrase "approaching a target point" may be that at the target point, an individual dose is applied, or the application of the individual dose is planned. A nonhomogeneous dose distribution may be simple to apply in this way. For example, a target point, for which a higher total dose is intended, may be approached more often during the rescanning passes than a target point, for which a smaller total dose is intended.

Because the target points of the target region are approached variously often, the results is that in certain rescanning passes, at least some of the target points are not approached. For example, if a total of 10 rescanning passes is intended, but one target point is to be approached a total of only 10 times in all, then there are three rescanning passes, in which the target point is not approached (e.g., skipped).

It is advantageous if the approaches of the target points are divided up among the rescanning passes such that before a final rescanning pass, in which at least one target point that is not approached in every rescanning pass is approached, there is at least one further rescanning pass, in which the at least one target point is not approached. This may be attained, for example, in that in the first rescanning pass, the at least one target point is not approached. However, this may also be attained in that for one target point that is approached in at least two rescanning passes, there is at least one further rescanning pass, in which the one target point is not approached, in between the two rescanning passes.

It is advantageous if the target points are approached variously often in the rescanning. This makes it possible to provide a nonhomogeneous dose application and at the same time, to provide that no individual dose that is applied to a target point becomes so small that secure monitoring of the application of the individual dose by the measuring instruments may no longer be provided.

It is problematic if in repeated rescanning passes, the target points are approached until such time as a total dose per target point has been applied, and the target points are no longer approached in subsequent rescanning passes. This "rigid" scheme thins out the quantity of target points that are approached in a rescanning pass. However, this is disadvantageous for an irradiation system. If in a later rescanning pass, in which the target points have been thinned out, the beam must therefore be interrupted too often (e.g., to proceed from a remaining island of target points to the next remaining island), this increases the irradiation time.

This rigid scheme is opened up by the present planning method. As a result, the irradiation of one target point may be shifted to a later time (e.g., to a later rescanning pass). This makes it possible to lessen or avoid the adverse effects described.

For example, a target point that is first approached in a later rescanning pass may be used to connect the remaining islands of the later rescanning pass. As a result, the beam path that is traversed during the later rescanning pass may be flexibly optimized. Despite the fact that a plurality of target points is typically used to connect the remaining islands of a later rescanning pass, an individual target point that is not approached until a later rescanning pass may lead to an improved embodiment of the rescanning passes, depending on a constellation of a target region geometry and on the dose distribution to be applied.

The target points to be approached during the rescanning passes may, however, also be divided up such that the number of target points to be approached per rescanning pass is distributed as uniformly as possible (e.g., the number of target points that are approached in each pass is essentially the same). This essentially uniform distribution has the effect that "thinning out" occurs to only a limited extent, if at all.

This may be achieved, for example, by having one or more target points in each rescanning pass that are not approached. The target points and the number of approaches per target point may be distributed statistically over the rescanning passes.

One example of dividing up the target points among the rescanning passes is to do the distribution or dividing up with regard to the scanning path, such that a scanning path, by which the target points to be approached are approached meets a predefined criterion in one of the rescanning passes. If the predefined criterion is not met, then the distribution of the target points may be changed. The distribution may also be designed from the outset such that for the algorithm to be executed, certain combinations of target points and rescanning passes are not allowed.

The predefined criterion may, for example, be that in a scanning path, a spacing between two target points to be approached successively is below a threshold value. For example, it may be specified that the maximum spacing between two target points is less than 20 mm (e.g., less than 10 mm or less than 5 mm). In that case, the scanning may be done without absolutely requiring a shutoff of the beam between the two target points. Other possible criteria may be that the number of required interruptions in the beam on traversing the scanning path is minimized or is below a threshold value.

In one embodiment, the planning process is designed such that for one target point, the total dose to be applied is an integral multiple of the individual dose to be applied at that target point. The individual dose is always applied whenever the target point is approached in a rescanning pass. This restriction has the advantage that at every target point, the total individual dose may always be applied. The application of fractions of the individual dose, which is also problematic, since it may not be possible for the application of fractions to be monitored with the requisite accuracy, is thereby avoided.

This embodiment may be implemented independently of the method disclosed. This provides that in the rescanning, or in irradiation planning for a rescanning pass, only ratios between the total dose and the individual dose that are integers are allowed per target point. Per target point, the total individual dose is applied. Such an embodiment may be implemented, for example, by specifying boundary conditions that limit the degrees of freedom in determining the irradiation parameters. For example, the three-dimensional location of the target points may also be selected such that this prerequisite may be met. The individual dose that is the basis of the integral ratio may be selected to be the same for the entire irradiation plan or for different portions of the irradiation plan, as is true for different target regions as well.

The individual dose may be selected as small enough that the individual dose is still just above a threshold value. As a result, it may be provided that the dose application may be monitored accurately. If an individual dose is to become too small, it may no longer be possible for the measuring instruments to monitor the individual dose with the requisite accuracy. In the final analysis, this may endanger the success of the treatment.

Independently of the methods disclosed, the individual dose to be applied at a target point (e.g., the dose that is applied upon an approach to the target point such as in rescanning) may be selected such that the individual dose is always above a predetermined threshold value. The individual dose may thus still be monitored with the requisite accuracy by the same measuring instruments, with which the dose application is measured. The individual dose may be adapted to the choice of the measurement range of the measuring instruments and to the extracted intensity from the accelerator. The capability of the hardware used is explicitly taken into account. If in the course of the irradiation the hardware is operated by a different mode of operation (e.g., with an altered extracted intensity and/or with a different choice of the measurement range of the detector), the predetermined threshold value may be adapted accordingly.

The individual dose within this specification may be selected to be as small as possible, since then the number of rescanning passes is increased, and thus the favorable effects of the rescanning are more pronounced. The specification that the "total dose is an integral multiple of the individual dose" may be met more easily. For example, the individual dose may be below ten or five times the threshold value (e.g., below twice the threshold value). Irradiation planning devices and control devices for irradiation systems may be embodied accordingly.

In one embodiment, an individual dose of equal size is applied at each of the target points of the target region. This embodiment is well suited for being installed in an irradiation system because an irradiation system may be designed and optimized for the equal-size individual dose to be applied. For example, the measurement ranges of the devices, with which the application of the individual dose is monitored, may be adapted to the size of the irradiation system. In rescanning (e.g., volumetric rescanning), the irradiation may be done without switching over isoenergy layers, without switching over the intensity, with which the particle beam is extracted from the accelerator unit, and/or without switching over the measurement ranges of the measuring devices (e.g., of the ionization chamber system), which results in an individual dose of equal size.

In the process, it is unnecessary to scan the entire target region with all the rescanning passes before making a transition to a further target region of the target volume that is irradiated with different rescanning passes. Even during some of the rescanning passes, with which one target region is irradiated, target points of a different target region may be approached. By this "weaving" of the rescanning passes for one target region with the rescanning passes of the other target region, an advantageous approach to the target points may be achieved. If in one rescanning pass, only a few target points of a target region are to be approached, for example, then the few target points may also be accommodated in a different rescanning pass of the other target region. It is also advantageous not to traverse some of the target points of a target region until the irradiation of another target region has already begun. This method may be implemented independently of the methods disclosed. Irradiation planning devices and control devices for irradiation systems may be embodied accordingly.

The method for irradiating a target region in a target volume is configured such that the target region includes target points that are to be approached individually. In the target region, a nonhomogeneous dose distribution is applied, for example. The target region is irradiated with a plurality of rescanning passes (e.g., the target region is scanned multiple times in all). The target points of the target region are approached variously often during the rescanning passes, so that at least some of the target points are not approached in every rescanning pass. The method is configured such that at least one target point that is not approached in every rescanning pass, prior to a final rescanning pass, in which the at least one target point is approached, at least one further rescanning pass, in which the at least one target point is not approached, is performed.

One embodiment of an irradiation planning device has a computer unit that is configured for performing one of the methods disclosed for irradiation planning. This may be done, for example, with the aid of a suitable computer program.

One embodiment of a control device for an irradiation system has a control computer that controls an irradiation system during an irradiation such that one of the methods disclosed is performed for irradiating a target region in a target volume. This too may be done with a suitable computer program. The irradiation system of the present embodiments has a control device of this kind.

Embodiments and advantages discussed and explained for the method for irradiation planning also apply to the method for irradiating a target region in a target volume, and correspondingly to the irradiation planning device and to the control device for an irradiation system.

BRIEF DESCRIPTION OF THE DRAWINGS

FIG. 8 is a flowchart of one embodiment of a method for irradiating a target volume.

DETAILED DESCRIPTION OF THE DRAWINGS

Figure 1:
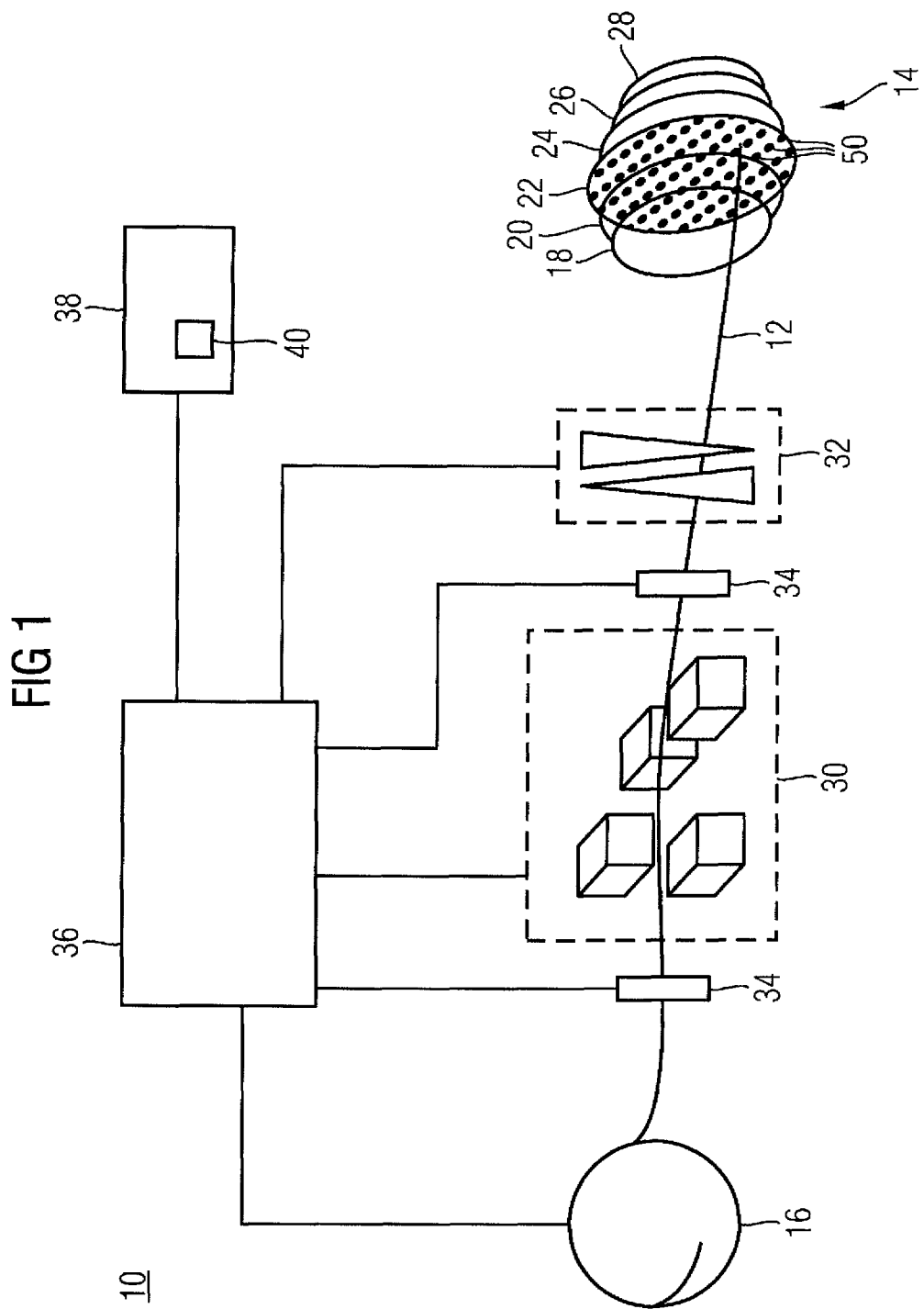
FIG. 1 shows one embodiment of an irradiation system, with which a rescanning process is performed.

FIG. 1, in a schematic illustration, shows a layout of a particle therapy system 10. The particle therapy system 10 is used for irradiating a body located on a positioning device with a beam of particles (e.g., a particle beam 12). For example, as a target volume 14, a tumor-diseased tissue of a patient may be irradiated with the particle beam 12. The particle therapy system 10 may be used for irradiating a inanimate body (e.g., a water phantom or some other phantom). Irradiating the water phantom may be done, for example, for the sake of checking and verifying irradiation parameters before and/or after an irradiation of a patient is done. Other bodies (e.g., experimental constructions such as cell cultures or bacterial cultures) may be irradiated with the particle beam 12 for research purposes.

The particle therapy system 10 may include an accelerator unit 16 (e.g., a synchrotron, cyclotron, or other accelerator) that furnishes a particle beam 12 with the requisite energy for the irradiation. As the particles, particles such as protons, pions, helium ions, carbon ions, or ions of other elements may be used. In one embodiment, the particle beam 12 has a beam diameter of 3-10 mm width.

In the target volume 14 to be irradiated, layers 18, 20, 22, 24, 26 and 28 that are equivalent to isoenergy layers are indicated. An isoenergy layer 18, 20, 22, 24, 26 or 28 is characterized by a penetration depth of the particle beam 12, at a defined energy of the particle beam 12. Each of the isoenergy layers 18, 20, 22, 24, 26, 28 in the example shown in FIG. 1 represents one target region within the target volume 14 that is to be irradiated in the rescanning process.

A raster scanning process, in which the particle beam 12 is guided from target point 50 to target point 50 without a compulsory shutoff at a transition from one target point 50 to the next, may be employed. Spot-scanning processes with a shutoff of the particle beam 12 between the individual target points 50, or other scanning processes such as a continuous scanning process, may also be employed for irradiating the target region by a rescanning process. In FIG. 1, several target points 40 in a middle isoenergy layer 22 in the target volume 14, which are approached successively by the particle beam 12, are shown.

The particle beam 12 shown in FIG. 1 is varied in a lateral deflection with the aid of scanning magnets 30. The particle beam 12 is deflected in a direction (e.g., the X and Y direction) perpendicular to the direction, in which the particle beam 12 extends. An energy modulation device 32, with which an energy of the particle beam 12 may quickly be changed so that a penetration depth of the particle beam 12 may be varied, may be provided. Rescanning in the beam direction of the particle beam 12 may also be provided (e.g., volumetric rescanning; the beam path need not extend within an isoenergy layer).

The irradiation system 10 also includes a flow controller 36 and detectors 34 for monitoring beam parameters. The disposition of the components of the particle therapy system 10 shown in FIG. 1 is merely an example. Fixtures in a different disposition may also be provided.

The flow controller 36 (e.g., a control system of the irradiation system) controls the individual components of the system (e.g., the accelerator 16 and the scanning magnets 30) and collects measurement data such as data from the detectors 34 for monitoring the beam parameters. The control may be effected based on an irradiation plan 40 that is ascertained and furnished with the aid of an irradiation planning device 38.

In the particle therapy system 10 shown in FIG. 1, embodiments may be implemented. Embodiments are described in further detail in conjunction with the next drawing.

The target volume 14 in FIG. 1 has an ellipsoid shape. If the target volume 14 is to be irradiated as a whole with a homogenous set-point dose, this provides that a dose distribution to be applied in a middle isoenergy layer 22 is nonhomogeneous. This is due to a central region of the middle isoenergy layer 22 already being exposed to a slight dose when the isoenergy layers 24, 26, 28 located downstream of the middle isoenergy layer 22 are irradiated. For the middle isoenergy layer 22, the dose to be applied is therefore greater at an edge than in the center.

Figure 2:
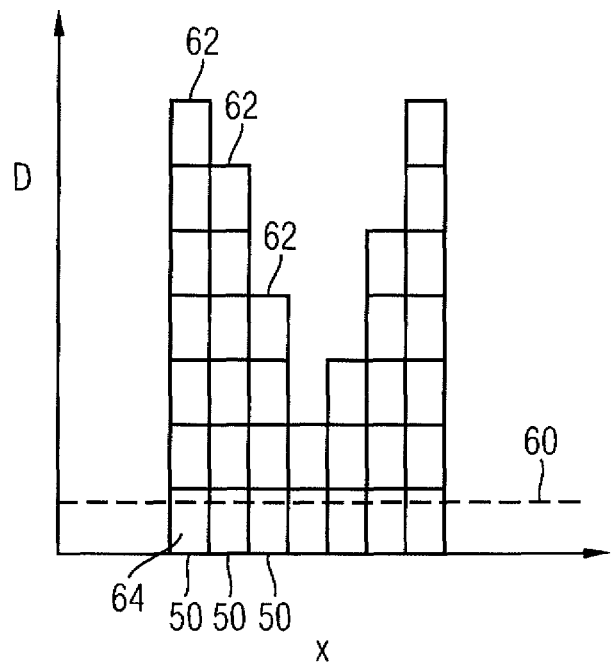
FIG. 2 is a graph showing a nonhomogeneous dosage distribution that is to be applied in an isoenergy layer.

The dose distribution to be applied in the middle isoenergy layer 22 is shown in FIG. 2 for some target points in the middle isoenergy layer 22. The X axis identifies a site x of the target points along a line inside the middle isoenergy layer 22; the Y axis identifies a total dose D to be applied.

In dashed lines, a threshold value 60 that indicates a minimal fluence, and by way of the threshold value 60, also a minimal dose to be applied, is shown. The application of the minimal fluence may be monitored with requisite accuracy by measuring instruments of the particle therapy system 10.

A nonhomogeneous total dose 62 to be applied for the middle isoenergy layer 22 is selected such that the total dose 62 to be applied at each of the target points 50 is always an integral multiple of one individual dose 64. This choice may be made during the irradiation planning and therefore may be possible, since the individual dose 64 is selected to be so small that the individual dose 64 is just above the threshold value 50 and thus may be markedly less than the total dose 62 to be applied. The individual dose 64 may, for example, be less than 1.5 times the threshold value 60. The choice of the individual dose 64 provides that the dose application may be monitored with the requisite accuracy, and as many rescanning passes as possible may be made in order to apply the total dose 62 for the middle isoenergy layer 22.

The isoenergy layer is irradiated in the rescanning process. In this process, during the various rescanning passes, a target point 50 is approached until the total dose 62 for the target point 50 has been reached. Upon each approach to a target point 50, the total individual dose 64 may be applied, because of the integral ratio.

Specifying the individual dose has the effect that proximal layers, which may be irradiated with a lesser dose, since the proximal layers are coated with a preliminary dose, are irradiated with fewer rescanning passes. These regions have already been irradiated indirectly in many rescanning passes by the irradiation of distal layers. Settings in the proximal layers that allow more-accurate dosage measurement and accordingly lower threshold values 60 are used. This may be attained, for example, by way of a lesser intensity of the particle beam and by the choice of a more-sensitive measurement range of the measuring devices (e.g., ionization chambers), with which the dose application of the particle beam is monitored.

With the aid of FIGS. 3-8, an embodiment of a method for irradiating a target volume is explained on the basis of the illustration of a fictive quadratic isoenergy layer 52. The isoenergy layer 52 shown is a simplification of an isoenergy layer that may occur in reality. The basic principle may be better explained this way.

Figure 3:
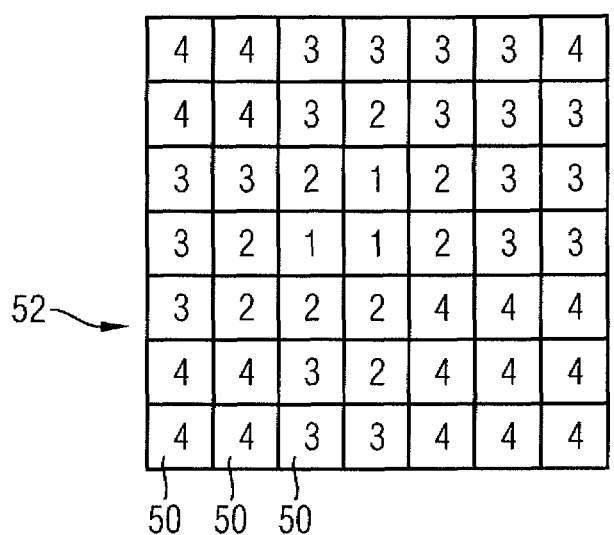
FIG. 3 is a dose distribution to be applied in a target region.
Figure 4:
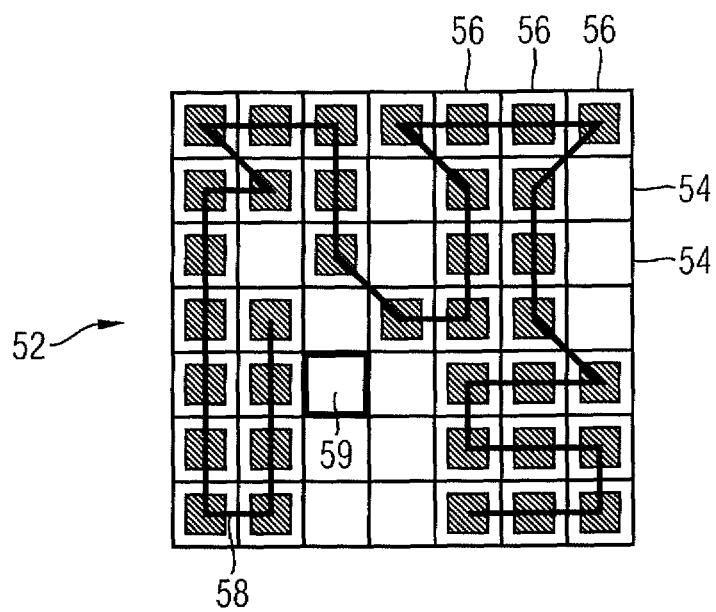
FIGS. 4-7 show four rescanning passes to be performed successively, with an illustration of the target points that are approached in each rescanning pass.
Figure 5:
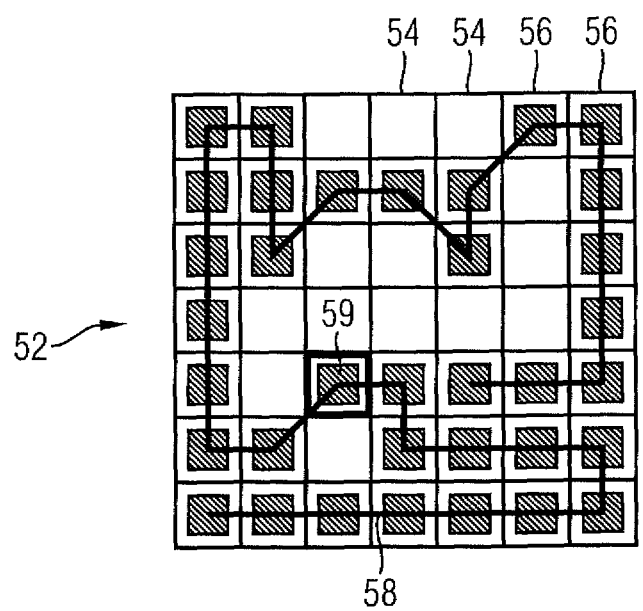
Figure 6:
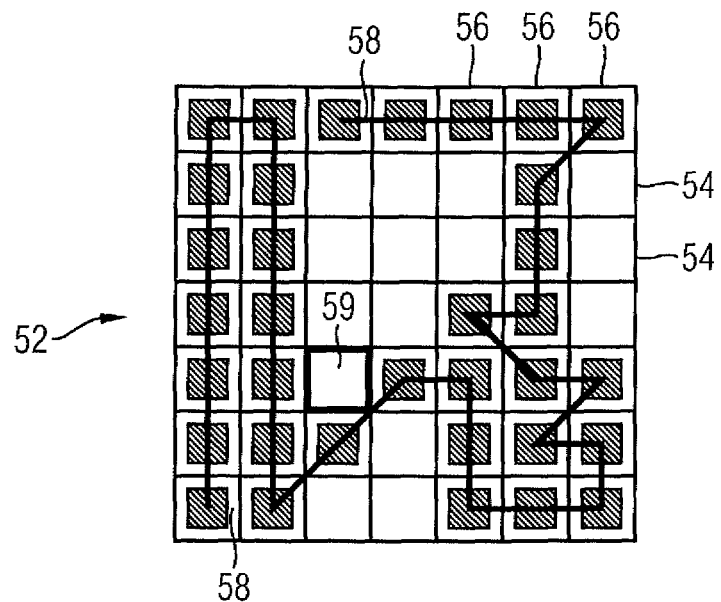
Figure 7:
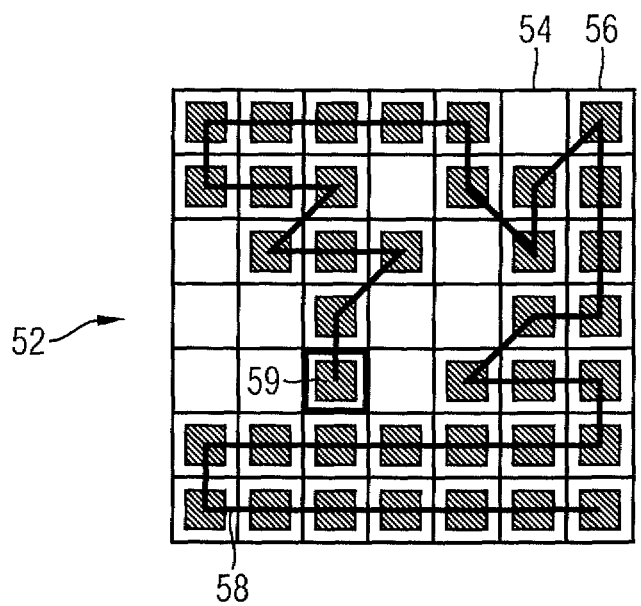

FIG. 3 shows the total dose to be applied to each target point 50 in the form of a multiple of one individual dose. The total dose is greater in peripheral regions of the quadratic isoenergy layer 52 (e.g., up to 4 times the individual dose) than in the center (e.g., only 1 times the individual dose). This is approximately equivalent to the nonhomogeneous dose distribution shown in FIG. 2.

FIGS. 4-7 show the approach of the target points for four rescanning passes to be performed successively. An occupied box 56 provides that the target point is approached in the corresponding rescanning pass, and that the individual dose is applied at the target point. An unoccupied box 54 provides that the target point is not approached (i.e., is excluded) in the rescanning pass.

The target points 50 are distributed among the rescanning passes such that in every rescanning pass, as constant as possible, a number of target points 50 is approached. Also, in the distribution of the target points 50 among the rescanning passes, a continuous scanning path may always be found, so that an irradiation is possible in one rescanning pass without an interruption.

The uniform distribution provides, for example, that for certain target points, there are rescanning passes, in which the target point is not approached. The rescanning passes are located before a rescanning pass, in which that target point is approached. This is the case for one of the central target points 59, for example. That target point 59 is approached in only the second and fourth rescanning passes, but not in the first and third rescanning passes.

For example, the distribution provides that some target points are not approached until later rescanning passes. Favorable scanning paths 58 may be found. As methods for this, known algorithms of the kind also used for general traveling-salesman problems may be employed. In the case of complex target regions of the kind that occur in reality, it may happen that noncohesive islands of target points have to be approached in a rescanning pass. This may be avoided by the described dividing up of the approaches to the target points among different rescanning passes.

FIG. 8 shows a schematic illustration of the method acts that are performed in the planning of an irradiation by the rescanning process.

A target volume is defined in an object to be irradiated (act 70). The target volume is divided into target regions that are each to be irradiated in a plurality of rescanning passes (act 72).

For each of the target regions, a dose distribution to be applied is ascertained (act 74). In the process, an individual dose that describes the dose that is administered in one target point per approach to the target point may be determined. The individual dose may also be defined from the outset instead. Ascertaining the dose distribution to be applied may also be done under certain peripheral conditions. For example, it may be specified that per target point, the total dose to be applied is an integral multiple of one individual dose. From the individual dose and from the total dose per target point, the number of rescanning passes that are to be applied in order to apply the desired dose distribution in the target region may be obtained.

The target points and the approach to the target points are divided up among the rescanning passes, for example, such that at least one target point that is not approached in every rescanning pass, there is at least one rescanning pass prior to the final approach to the at least one target point, during which the at least one target point is not approached (act 76).

Once the approaches to the target points have been distributed among the rescanning passes, a check is made as to whether the target points may be approached in every rescanning pass by a scanning path that meets predefined criteria (act 78). For example, whether the number of interruptions in the beam that are required in executing a scanning path are below a value or are minimized may be checked.

If the predefined criteria are not met, then the distribution of the target points and the approach to the target points may be changed, for example, such that the resultant scanning paths meet the predefined criteria better.

The distribution of the target points to rescanning passes is repeated in a similar way for each target region. The irradiation of the target region or of target regions of the target region may be done in accordance with the irradiation planning.

The method can be combined with other methods that pertain to rescanning. For example, the rescanning passes may be laid out chronologically such that desynchronization of the motion of the target volume occurs. The method may be combined with a method as disclosed in US Patent Application 2008/0078942 A1.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for irradiation planning for a target volume, the method comprising:
   defining, with a computer unit, a target region having a plurality of target points, the plurality of target points being individually approachable;
   defining, with the computer unit, a number of rescanning passes, in which the target region is scanned multiple times, such that the plurality of target points of the target region is approached variously often during the rescanning passes, so that at least some target points of the plurality of target points are not approached in each rescanning pass;
   generating an irradiation plan based on the defined rescanning passes; and
   sending the generated irradiation plan to an irradiaiton system, the generated irradiation plan being executable by the irradiation system,
   wherein the approaching of the plurality of target points is distributed among the rescanning passes such that for at least one target point of the plurality of target points that is not approached in each rescanning pass, at least one further rescanning pass, in which the at least one target point is not approached, is located before a final rescanning pass, in which the at least one target point is approached.

2. The method as defined by claim 1, wherein a target point of the plurality of target points is not approached in a first rescanning pass.

3. The method as defined by claim 2, wherein for a target point of the plurality of target points that is approached in at least two of the rescanning passes, the at least one further rescanning pass, in which the at least one target point is not approached, is located between the at least two rescanning passes.

4. The method as defined by claim 1, wherein for a target point of the plurality of target points that is approached in at least two of the rescanning passes, the at least one further rescanning pass, in which the at least one target point is not approached, is located between the at least two rescanning passes.

5. The method as defined by claim 4, wherein in each of the rescanning passes, some target points of the plurality of target points are not approached.

6. The method as defined by claim 1, wherein in each of the rescanning passes, some target points of the plurality of target points are not approached.

7. The method as defined by claim 1, wherein the approach to the plurality of target points is distributed among the rescanning passes such that a scanning path, by which target points to be approached in one of the rescanning passes are approached, meets a predetermined criterion.

8. The method as defined by claim 7, wherein the predetermined criterion includes that in the scanning path, a spacing between two target points of the plurality of target points to be approached successively is below a threshold value.

9. The method as defined by claim 8, wherein at the plurality of target points of the target region, an equal-sized individual dose is applied upon each approach of the rescanning passes.

10. The method as defined by claim 7, wherein at one target point of the plurality of target points, a total dose to be applied is an integral multiple of an individual dose to be applied at the one target point.

11. The method as defined by claim 1, wherein at one target point of the plurality of target points, a total dose to be applied is an integral multiple of an individual dose to be applied at the one target point.

12. The method as defined by claim 11, wherein the individual dose is selected as a multiple of a threshold value, the threshold value being specified by a measuring device for monitoring a particle beam property.

13. The method as defined by claim 1, wherein at the plurality of target points of the target region, an equal-sized individual dose is applied upon each approach of the rescanning passes.

14. A method for irradiating a target region in a target volume, the target region including a plurality of target points to be approached individually, the method comprising:
   irradiating the target region by a plurality of rescanning passes, by which the target region is scanned multiple times;
   approaching the plurality of target points of the target region variously often during the plurality of rescanning passes, at least part of the target region not being scanned in each rescanning pass of the plurality of rescanning passes; and
   performing at least one further rescanning pass, in which at least one target point of the plurality of target points that is not approached in every rescanning pass of the plurality of rescanning passes is not approached, prior to a final rescanning pass, in which the at least one target point is approached.

15. The method as defined by claim 14, wherein the at least one target point is not approached in a first rescanning pass, or wherein the at least one target point is approached in at least two rescanning passes, such that between the at least two rescanning passes, at least one further rescanning pass, in which the at least one target point is not approached, is performed.

16. The method as defined by claim 15, wherein at a further target point of the plurality of target points, a total dose to be applied is applied as a multiple of an individual dose to be applied at the further target point.

17. The method as defined by claim 14, wherein at one target point of the plurality of target points, a total dose to be applied is applied as a multiple of an individual dose to be applied at the one target point in one of the rescanning passes.

18. An irradiation planning device comprising:
   a computer unit configured to:
      define a target region having a plurality of target points, the plurality of target points being individually approachable;
      define a number of rescanning passes, in which the target region is scanned multiple times, such that the plurality of target points of the target region is approached variously often during the rescanning passes, at least some target points of the plurality of target points not being approached in each rescanning pass;
      generate an irradiation plan based on the defined rescanning passes; and
      send the generated irradiation plan to a control device for an irradiation system, the control device for the irradiation system operable to control the irradiation system based on the generated irradiaton plan,
   wherein the approachment of the plurality of target points is distributed among the rescanning passes such that for at least one target point of the plurality of target points that is not approached in all of the rescanning passes, at least one further rescanning pass, in which the at least one target point is not approached, is located before a final rescanning pass, in which the at least one target point is approached.

19. A control device for an irradiation system, the control device comprising:
   a control computer, the control computer, in an irradiation, being configured to control the irradiation system such that the irradiation system is configured to:
      irradiate the tar et re ion b a slurality of rescanning passes, by which the target region is scanned multiple times;
      approach the plurality of target pointshe target region variously often during the plurality of rescanning passes, at least part of the target region not being scanned in each rescanning pass of the plurality of rescanning passes; and
      perform at least one further rescanning pass, in which at least one target point of the plurality of target points that is not approached in every rescanning pass of the plurality of rescanning passes is not approached, prior to a final rescanning pass, in which the at least one target point is approached.

20. An irradiation system comprising:
   an accelerator unit; and
   a control device comprising:
      a control computer, the control computer, in an irradiation, being configured to control the irradiation system such that the control computer is configured to:
         define a target region having a plurality of target points, the plurality of target points being individually approachable;
         define a number of rescanning passes, in which the target region is scanned multiple times, such that the plurality of target points of the target region is approached variously often during the rescanning passes, at least some target points of the plurality of target points not being approached in all of the rescanning passes; and
         control the accelerator unit based on the defined rescanning passes,
      wherein the approachment of the plurality of target points is distributed among the rescanning passes such that for at least one target point of the plurality of target points that is not approached in all of the rescanning passes, at least one further rescanning pass, in which the at least one target point is not approached, is located before a final rescanning pass, in which the at least one target point is approached.

21. The irradiation system as defined by claim 20, wherein the control computer comprises a flow controller and an irradiation planning device.

* * * * *